United States Patent [19]

Horii et al.

[11] 3,961,049
[45] June 1, 1976

[54] METHOD FOR CONTROLLING MITES AND THIOUREIDOBENZENE PHOSPHATES

[75] Inventors: Tetsuo Horii; Isao Chiyomaru, both of Shimizu; Seigo Kawada, Fujieda; Kiyoshi Takita, Shimizu, all of Japan

[73] Assignee: Kumiai Chemical Industry Co., Ltd., Tokyo, Japan

[22] Filed: Jan. 10, 1975

[21] Appl. No.: 540,227

Related U.S. Application Data

[62] Division of Ser. No. 349,175, April 9, 1973, Pat. No. 3,903,271.

[30] Foreign Application Priority Data

Apr. 18, 1972 Japan............................... 47-39020

[52] U.S. Cl................................. 424/211; 260/938
[51] Int. Cl.².................... C07F 9/165; A01N 9/36
[58] Field of Search.................... 260/938; 424/211

[56] References Cited
UNITED STATES PATENTS

| | | | |
|---|---|---|---|
| 2,494,126 | 1/1950 | Hoegberg............................ | 260/938 |
| 3,420,918 | 1/1969 | Fancher et al...................... | 260/938 |
| 3,903,271 | 9/1975 | Horii et al......................... | 260/938 X |

*Primary Examiner*—Anton H. Sutto
*Attorney, Agent, or Firm*—Stevens, Davis, Miller & Mosher

[57] ABSTRACT

Novel thioureidobenzene compounds having the general formula

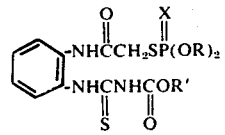

wherein R and R' are lower alkyl groups and X is oxygen or sulfur atom is prepared by reacting a compound having the general formula

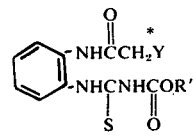

wherein Y is chlorine or bromine, with a compound having the general formula

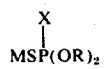

wherein M is ammonium or an alkali metal. These compounds have high miticidal and fungicidal activity.

8 Claims, No Drawings

METHOD FOR CONTROLLING MITES AND THIOUREIDOBENZENE PHOSPHATES

This is a division of application Ser. No. 349,175, filed Apr. 9, 1973, now U.S. Pat. No. 3,903,271.

The present invention relates to novel thioureidobenzene series compounds having the general formula

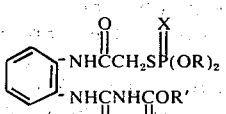

wherein R and R' shows lower alkyl groups and X shows oxygen or sulfur atom, a method for producing said compounds, a method for using said compounds and miticial and fungicidal compounds containing said compounds as an active ingredient.

The thioureidobenzene series compounds of the present invention show a high activity for protecting *Tetranichus telarius* and also protecting rice plant diseases, such as rice blast (*Piricularia oryzae*), sheath bright (*Pellicularia sasaki*) and the like; vegetable diseases, such as *Selerotinia sclerotiorum*, *Colletotrichum lagenarium* (cucumber) and the like and fruit diseases, such as *Elsinoe fawcetti* and *Diaporthe citri* in oranges, *Venturia pirina* (pear) and the like.

For controlling mites and diseases for agricultural horticultural plants, various pesticides have been developed and used practically but pesticides capable of being satisfied in view of fungicidal activity and phytotoxicity are few. Furthermore, the use of pesticides have been recently very severely regulated in view of the residual toxicity or chronic toxicity as well as the acute toxicity and there have been few safely usuable pesticides. Accordingly, the inventors have synthesized a large number of organic compounds and repeated tests for physiological activity. By such tests it has been found that the compounds of the present invention have excellent miticidal and fungicidal activities and are effective for controlling a variety of mites and diseases.

As the already known thioureidobenzene series compounds, Japanese Pat. No. 594,330 has disclosed the compounds having the general formula

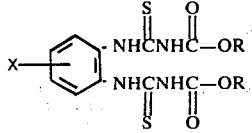

wherein X is hydrogen, nitro group, halogen atom or a lower alkyl group and R is a lower alkyl group.

However, the compounds according to the present invention containing a phosphorus atom are novel and have far higher activity than these already known compounds and have no phytotoxicity and no toxicity against human bodies and domestic animals and can be safely used.

The compounds according to the present invention can be produced by the following reaction formula

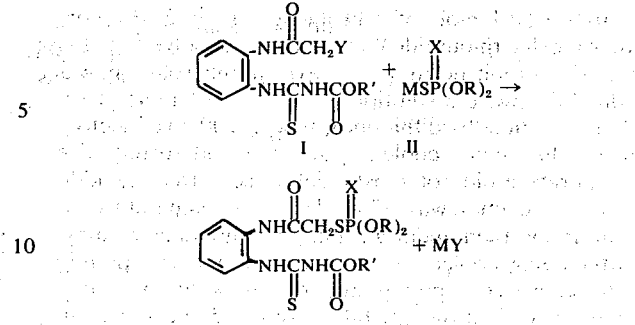

In the above formulae, R, R' and X have the same meanings as described above and Y shows chlorine or bromine atom and M is ammonium or an alkali metal.

Namely, the above compound (I) and compound (II) are reacted in a solvent of alcohols, such as methanol, ethanol, butanol; ketones, such as acetone, methyl ethyl ketone; aliphatic hydrocarbons, such as petroleum ether, ligroin, hexane; aromatic hydrocarbons, such as benzene, toluol, xylol; ethers, such as ethyl ether, dioxane; esters, such as methyl acetate, ethyl acetate, dimethylformamide, dimethylacetamide, dimethylsulfoxide and the like. The reaction temperature is 0°–100°C, preferably 50°–80°C and the reaction time is 1–10 hours. From the economic point, the reaction time is sufficient after 3–4 hours. It is preferred to add equivalent or a slightly excess amount of the compound (II) based on the compound (I).

The purification may be effected by recrystallizing the synthesized compound from an alcohol-water system.

An explanation will be made with respect to the synthesis of the compounds of the present invention.

EXAMPLE 1

1-diisopropoxyphosphinylthioacetamido-2-(3-methoxycarbonyl-2-thioureido)benzene

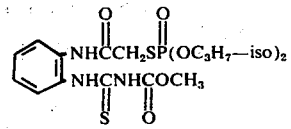

30.1 g (0.1 mol) of 1-chloroacetamido-2-(3-methoxycarbonyl-2-thioureido)benzene and 23.6 g (0.1 mol) of potassium o,o-diisopropylthiophosphate were mixed and dissolved in 250 ml of acetone and the resulting solution was reacted at room temperature for 1 hour and further under a reflux for 2 hours by heating. After cooling, the formed solid was filtered off and the filtrate was condensed under a reduced pressure. The precipitated solid was thoroughly crushed and then washed with water and dried. Thereafter, the obtained product was recrystallized from benzene to obtain 36.8 g of white powdery crystal having a melting point of 122°–124°C. The yield was 79.5%.

EXAMPLE 2

1-dimethoxyphosphinothioylthioacetamido-2-(3-methoxycarbonyl-2-thioureido)benzene

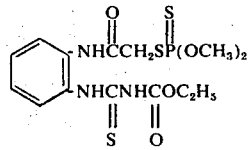

36.0 g (0.1 mol) of 1-bromoacetamido-2-(3-ethoxycarbonyl-2-thioureido)benzene was dissolved in 300 ml of acetonitrile and to the resulting solution was added dropwise a solution of 18.0 g (0.1 mol) of sodium o,o-dimethyldithiophosphate in 100 ml of acetonitrile while being cooled with water and stirred. The temperature did not substantially rise. After the addition, the reaction was effected at room temperature for 1 hour and then under a reflux for 2 hours by heating. After being cooled the reaction solution was poured into ice water to precipitate crystals, which were collected and then the crystals were dried and recrystallized from a mixture solvent of benzene and hexane to form 37.1 g of white powdery crystals having a melting point of 106°–108°C. The yield was 84.9%.

EXAMPLE 3

1-di-n-propoxyphosphinothioylthioacetamido-2-(3-methoxycarbonyl-2-thioureido)benzene

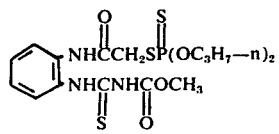

30.1 g (0.1 mol) of 1-chloroacetamido-2-(3-methoxycarbonyl-2-thioureido)benzene and 25.3 g (0.1 mol) of potassium o,o-di-n-propyldithiophosphate were mixed and dissolved in 500 ml of acetone and the resulting solution was reacted under reflux by heating for 3 hours while stirring. After being cooled, the formed solid was filtered off and the filtrate was condensed under a reduced pressure. The resulting precipitates were recrystallized from a solution of methyl alcohol and water in a mixture ratio of 3:1 to obtain 42.7 g of white powdery crystal having a melting point of 98°–100°C. The yield was 89%.

In the same manner, the following compounds are produced.

| Compound No. | Structure | Chemical name | MP °C (BP) | Appearance |
|---|---|---|---|---|
| 1 | ⌬-NHCCH₂SP(OCH₃)₂ (O,O) / NHCNHCOCH₃ (S,O) | 1-dimethoxyphosphinyl thioacetamido-2-(3-methoxycarbonyl-2-thioureido)benzene | 106–110 | light brown powdery crystal |
| 2 | ⌬-NHCCH₂SP(OCH₃)₂ (O,S) / NHCNHCOCH₃ (S,O) | 1-dimethoxyphosphinothioylthioacetamido-2-(3-methoxycarbonyl-2-thioureido)benzene | 115–119 | light brown powdery crystal |
| 3 | ⌬-NHCCH₂SP(OC₃H₇—iso)₂ (O,O) / NHCNHCOCH₃ (S,O) | 1-diisopropoxyphosphinyl-thioacetamido-2-(3-methoxycarbonyl-2-thioureido)benzene | 122–124 | white powdery crystal |
| 4 | ⌬-NHCCH₂SP(OC₃H₇—n)₂ (O,S) / NHCNHCOCH₃ (S,O) | 1-di-n-propoxyphosphinothioylthioacetamido-2-(3-methoxycarbonyl-2-thioureido)benzene | 98–100 | white powdery crystal |
| 5 | ⌬-NHCCH₂SP(OC₃H₇—iso)₂ (O,S) / NHCNHCOCH₃ (S,O) | 1-diisopropoxyphosphinothioylthioacetamido-2-(3-methoxycarbonyl-2-thioureido)benzene | 88–91 | light brown powdery crystal |
| 6 | ⌬-NHCCH₂SP(OC₃H₇—n)₂ (O,O) / NHCNHCOCH₃ (S,O) | 1-di-n-propoxyphosphinyl-thioacetamido-2-(3-methoxycarbonyl-2-thioureido)benzene | more than 140/0.1 mmHg | brown glutin-like substance |
| 7 | ⌬-NHCCH₂SP(OC₄H₉—n)₂ (O,O) / NHCNHCOCH₃ (S,O) | 1-di-n-butoxyphosphinyl-thioacetamido-2-(3-methoxycarbonyl-2-thioureido)benzene | more than 150/0.4 mmHg | brown glutin-like substance |
| 8 | ⌬-NHCCH₂SP(OC₄H₉—n)₂ (O,S) / NHCNHCOCH₃ (S,O) | 1-di-n-butoxyphosphinothioylthioacetamido-2-(3-methoxycarbonyl-2-thioureido)benzene | 85–87 | light brown powdery crystal |

-continued

| Compound No. | Structure | Chemical name | MP °C (BP) | Appearance |
| --- | --- | --- | --- | --- |
| 9 | ⌬-NHCCH$_2$SP(OC$_4$H$_9$—sec)$_2$ (O)(S)<br>  NHCNHCOCH$_3$ (S)(O) | 1-di-sec-butoxyphosphino-thioylthioacetamido-2-<br>(3-methoxycarbonyl-2-thioureido)benzene | 79–82 | light brown powdery crystal |
| 10 | ⌬-NHCCH$_2$SP(OCH$_3$)$_2$ (O)(S)<br>  NHCNHCOC$_2$H$_5$ (S)(O) | 1-dimethoxyphosphino-thioylthioacetamido-2-<br>(3-ethoxycarbonyl-2-thioureido)benzene | 106–108 | white powdery crystal |
| 11 | ⌬-NHCCH$_2$SP(OC$_2$H$_5$)$_2$ (O)(O)<br>  NHCNHCOC$_2$H$_5$ (S)(O) | 1-diethoxyphosphinyl-thioacetamido-2-(3-ethoxycarbonyl-2-thioureido)benzene | 98–101 | light brown prism-like crystal |
| 12 | ⌬-NHCCH$_2$SP(OC$_3$H$_7$—iso)$_2$ (O)(O)<br>  NHCNHCOC$_2$H$_5$ (S)(O) | 1-diisopropoxyphosphinyl-thioacetamido-2-(3-ethoxycarbonyl-2-thioureido)benzene | 107.5–111 | white powdery crystal |

When the compounds according to the present invention are used as a miticide or a fungicide, the compounds are mixed with a suitable carrier and formulated into wettable powder, dust, granule and emulsifiable concentrate. These compositions may be used directly or after being diluted with a diluent or mixed with other materials. Further, the compounds of the present invention can be used more widely by using them together with other fungicides and insecticides.

The carrier may be solid or liquid. When the carrier is used together with surfactants or dispersants, pesticidal compositions having more improved property can be obtained. As the solid carrier, use may be made of talc, diatomaceous earth, silica gel and other various materials. As the liquid solvent, use may be made of solvents ordinarily used for the preparation of pesticidal compositions, such as methyl ethyl ketone and other aliphatic compounds, and xylene and other aromatic compounds.

As the surfactants, use may be made of emulsifiers, such as polyoxyethylenealkylaryl ether, polyoxyethylenealkyl ether, polyoxyethylene aliphatic acid ester, alkylarylsulfonate, polyoxyethylenepolyalkyldiphenyl ether, etc. alone or in admixture; wetting agents, such as alkylarylsulfonate, polyoxyethylenealkylaryl ether, lauryl sulfate, polyoxyethylenealkylarylsulfonate, etc.; dispersants, such as ligninsulfonate, PVA, CMC, a condensate of alkylarylsulfonate with formaldehyde, etc.

The compound of the present invention is mixed with a solid carrier to prepare a dust. Further, the compound is mixed with a solid carrier and 1–3% of a surfactant as a wetting agent to prepare a wettable powder, which is diluted with water and used. The compound is added with a solvent and 5–15% of a surfactant as an emulsifier to prepare an emulsifiable concentrate, which is diluted with water to a suitable concentration and used. Furthermore, the compound can be mixed with a solid carrier, a surfactant and other adjuvants, and can be used in the form of a granule.

The invention will be further explained in detail with reference to the following examples for formulating various compositions. The additives and active ingredients can be varied within a wide range.

EXAMPLE 4

Wettable powder

Fifty parts (hereinafter, "parts" means by weight) of the above compound No. 2, 20 parts of diatomaceous earth, 25 parts of talc and 5 parts of a wetting agent, Sorpol (trademark, of a mixture of sodium dinaphthylmethanedisulfonate and sodium ligninsulfonate, made by Toho Kagaku Co.) were homogeneously mixed and milled to prepare a wettable powder.

EXAMPLE 5

Dust

Three parts of the above compound No. 1, 47 parts of talc, 47 parts of clay and 3 parts of white carbon were mixed and milled to prepare a dust.

EXAMPLE 6

Granule

Twenty parts of the above compound No. 4, 2 parts of sodium dodecylbenzenesulfonate and 78 parts of diatomaceous earth were homogeneously mixed and milled, and then kneaded together with 25 parts of water. The kneaded mixture was extruded through an extrusion type granule forming machine to obtain granules, which were dried and sieved to prepare a granule composition.

The excellent miticidal and fungicidal activities of the compounds of the present invention will be explained with respect to the following tests.

Test 1

Experiment of activity for preventing rice blast

An unglazed pot having a diameter of 2 cm planted with 20 plants of 4–5 leaf stage of yound rice plants (species: AICHI ASAHI) was mounted on a turntable and on the rice plants was sprayed a dispersion obtained by diluting the wettable powder according to the present invention prepared in the above Example 4 with water under a spraying pressure of 0.5 Kg/cm² by means of a spray gun in an amount of 30 ml per pot.

3 days after the spraying, a suspension of *Piricularia oryzae* spores in water formed by successively inoculating rice blast on rice plant in a greenhouse and adjusting the concentration of spores so as to contain 20 spores in a visual field (15×10 times) of a microscope, was sprayed on the rice plants in an amount of 5 ml per pot.

After the inoculation, the pot was placed in a wet room (saturated humidity, 24°C) made of vinyl sheet for 24 hours and then transferred into a greenhouse which was kept at a high temperature to propagate the diseased spots. Seven days after the inoculation, the number of diseased spots was counted with respect to 10 leaves per pot to calculate the protective value. The obtained results are shown in the following Table 1.

$$\text{Protective value (\%)} = \frac{(\text{Number of diseased spots in untreated pot}) - (\text{Number of diseased spots in treated pot})}{(\text{Number of diseased spots in untreated pot})} \times 100$$

Table 1

| Compound No. | Concentration (ppm) | Protective value (%) | Phytotoxicity |
|---|---|---|---|
| 1 | 250 | 96.8 | No |
| 2 | " | 100 | " |
| 3 | " | 94.7 | " |
| 4 | " | 100 | " |
| 5 | " | 100 | " |
| 6 | " | 98 | " |
| 7 | " | 99.2 | " |
| 8 | " | 100 | " |
| 9 | " | 100 | " |
| 10 | " | 100 | " |
| 11 | " | 95.1 | " |
| 12 | " | 99.2 | " |
| Blastin* | " | 95.2 | " |

*Pentachlorobenzylalcohol

Test 2

Experiment of activity for preventing sheath bright of rice plant

A pot having a diameter of 9 cm planted with three groups of 5–6 leaf stage rice plants (species: KINMAZE), one group of which has 3 plants was mounted on a turntable and on the rice plants was sprayed a dispersion obtained by diluting the wettable powder prepared in Example 4 with water under a spraying pressure of 1.0 Kg/cm² by means of a spray gun in an amount of 30 ml per pot. Next day the spraying, *Pellicularia sasaki* was inoculated on the thus treated rice plants. The inoculation of *Pellicularia sasaki* was conducted in the following manner. *Pellicularia sasaki* was cultured in a Petri dish containing potato agar medium for 3 days and then the medium was punched out into disks having a diameter of 10 mm. Then, the disk was inserted between the base portions of the rice plants to effect the inoculation. After the inoculation, the pot was maintained at a high temperature in a greenhouse for 10 days. Then the number of the diseased spots was counted with respect to 9 stems per pot to calculate the protective value according to the following formula.

$$\text{Protective value (\%)} = \left(1 - \frac{\text{Number of diseased spots in treated pot}}{\text{Number of diseased spots in untreated pot}}\right) \times 100$$

The obtained results are shown in the following Table 2.

Table 2

| Compound No. | Concentration (ppm) | Protective value (%) | Phytotoxicity |
|---|---|---|---|
| 1 | 125 | 100 | No |
| 2 | " | 98.2 | " |
| 3 | " | 99.1 | " |
| 4 | " | 98 | " |
| 5 | " | 100 | " |
| 6 | " | 100 | " |
| 7 | " | 97.6 | " |
| 8 | " | 100 | " |
| 9 | " | 100 | " |
| 10 | " | 99.4 | " |
| 11 | " | 97.8 | " |
| 12 | " | 100 | " |
| Neo-* asozine liquid composition | 32 | 98.8 | " |

*Consisting mainly of ferric ammonium salts of methanearsonic acid.

Test 3

**Experiment of activity for preventing *Selerotinia sclerotiorum* of haricot bean**

On 2 leaf stage haricot bean planted in an unglazed pot having a diameter of 15 cm was sprayed a dispersion obtained by diluting the wettable powder prepared in the above Example 4 with water in an amount of 15 ml. After one day, said bean plant was inoculated with a disk (diameter, 6 mm) of potato extract agar medium in which *Selerotinia sclerotiorum* had been cultured. 4 days after the inoculation, the morbidity was determined according to the following standard. The result is shown in the following Table 3.

Estimating standard of morbidity.

| | |
|---|---|
| 0: | Not diseased. |
| 1: | Diseased just under the inoculated portion or around said portion. |
| 2: | Diseased to about 1/5 of the inoculated leaves. |
| 3: | Diseased to about 2/5 of the inoculated leaves. |
| 4: | Diseased to about 3/5 of the inoculated leaves. |
| 5: | Diseased to about 4/5 of the inoculated leaves. |

$$\text{Protective value (\%)} = \left(1 - \frac{0 \times u_1 + 1 \times u_2 + \dots 5 \times u_5}{5 \times \epsilon u_i}\right) \times 100$$

$u_1-5$: Number of leaves of the estimating standard of morbidity.

Table 3

| Compound No. | Concentration (ppm) | Protective value (%) | Phytotoxicity |
|---|---|---|---|
| 1 | 250 | 91 | No |
| 2 | " | 93 | " |
| 3 | " | 84 | " |
| 4 | " | 82 | " |

Table 3-continued

| Compound No. | Concentration (ppm) | Protective value (%) | Phytotoxicity |
| --- | --- | --- | --- |
| 5 | '' | 68 | '' |
| 6 | '' | 92 | '' |
| 7 | '' | 91 | '' |
| 8 | '' | 96 | '' |
| 9 | '' | 93 | '' |
| 10 | '' | 86 | '' |
| 11 | '' | 91 | '' |
| 12 | '' | 90 | '' |
| Compound (A)* | '' | 21 | '' |

*Compound (A) 1,2-bis(3-ethoxycarbonyl-2-thioureido) benzene disclosed in Japanese Patent No. 594,330.

Test 4

Experiment of activity for preventing cucumber *Colletotrichum lagenarium*

When 15 seeds of cucumber (species: SAGAMI HANPAKU) were sown in an unglazed pot having a diameter of 4 cm and cotyledon appeared, a dispersion obtained by diluting the wettable powder prepared in the above Example 4 with water was sprayed on the cucumber seedlings under a spraying pressure of 1.0 Kg/cm² by means of a spray gun in an amount of 20 ml per pot while the pot being mounted on a turntable. After 24 hours, cucumber *Colletotrichum lagenarium* was sprayed and inoculated on the cucumber plants. *Colletotrichum lagenarium* had been cultured on corn agar medium for 10 days to obtain spores. Then, the spore concentration had been adjusted so as to contain 200 spores in a visual field (15×10 times) of a microscope. The thus formed spore suspension was sprayed on the cucumber plants in an amount of 4 ml per pot. After the inoculation, the pot was placed in a wet room (saturation humidity, 24°C) made of vinyl sheet for 48 hours and then transferred into a greenhouse and 7 days after the inoculation, the number of the diseased spots was determined. The number of the diseased spots was counted with respect to cotyledons of 10 cucumber seedlings and the protective value was calculated. The obtained results are shown in the following Table 4.

$$\text{Protective value (\%)} = \left(1 - \frac{\text{Number of diseased spots in treated pot}}{\text{Number of diseased spots in untreated pot}}\right) \times 100$$

Table 4

| Compound No. | Concentration (ppm) | Protective value (%) | Phytotoxicity |
| --- | --- | --- | --- |
| 1 | 250 | 100 | No |
| 2 | '' | 100 | '' |
| 3 | '' | 99.8 | '' |
| 4 | '' | 100 | '' |
| 5 | '' | 100 | '' |
| 6 | '' | 100 | '' |
| 7 | '' | 100 | '' |
| 8 | '' | 100 | '' |
| 9 | '' | 100 | '' |
| 10 | '' | 100 | '' |
| 11 | '' | 98.6 | '' |
| 12 | '' | 100 | '' |
| Compound (A) | '' | 90.8 | '' |

Test 5

Experiment of activity against adults or ova of *Tetranichus telarius*

1. Test for combating ova

The first leaf of haricot bean grown in a pot having a diameter of 10 cm was cut off in circular forms by a 3 cm leaf punch and 5 *Tetanichus telarius* adults were infested on each the cut circular leaf and allowed to be blown. The adults were removed 24 hours after the infesting in order to make the ova age to be uniform. The ova deposited leaf was immersed for 10 seconds in an aqueous dispersion obtained by diluting the wettable powder prepared in Example 4 with water into a given concentration. The percentage of combating ova was determined as follows. The number of ova was previously counted prior to the blowing and when all the ova in the untreated leaf were blown, the number of the blown ova was counted.

2. Test for combating adults

Haricot bean leaf in 2 stage was punched by a leaf punch and the punched leaf was immersed for 10 seconds in a dispersion obtained by diluting the wettable powder prepared in Example 4 with water into a given concentration and the immersed leaf was dried under air and infested with the adults. After 3 days, the number of the living adults was determined.

In both the tests for ova and adult, they were made in 2 replications in which one zone was 50 adults.

The obtained result is shown in the following Table 5.

Table 5

| Compound No. | Concentration (ppm) | Percentage of combating ova (%) | Percentage of combating adults (%) |
| --- | --- | --- | --- |
| 1 | 500 | 98.5 | 100 |
| 2 | '' | 100 | 100 |
| 3 | '' | 100 | 100 |
| 4 | '' | 98.5 | 100 |
| 5 | '' | 92.0 | 100 |
| 6 | '' | 95.8 | 100 |
| 7 | '' | 99.0 | 100 |
| 8 | '' | 100 | 100 |
| 9 | '' | 100 | 100 |
| 10 | '' | 100 | 99.2 |
| 11 | '' | 100 | 100 |
| 12 | '' | 100 | 100 |
| Untreated | — | 0 | 0 |

What is claimed is:

1. A method of controlling mites which comprises applying a miticidally effective amount of a thioureidobenzene compound having the formula

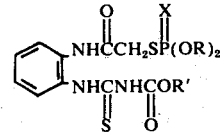

wherein R and R' are lower alkyl groups and X is oxygen or sulfur atom to plants.

2. A thioureidobenzene compound having the formula

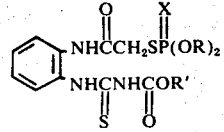

wherein R is an alkyl group having 1 to 4 carbon atoms, R' is methyl or ethyl and X represents oxygen or sulfur atom.

3. The thioureidobenzene compound as claimed in claim 2, which is

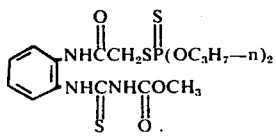

4. The thioureidobenzene compound as claimed in claim 2, which is

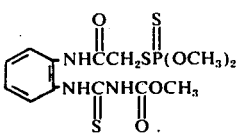

5. The thioureidobenzene compound as claimed in claim 2, which is

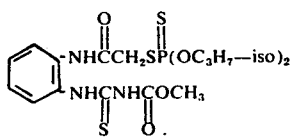

6. The thioureidobenzene compound as claimed in claim 2, which is

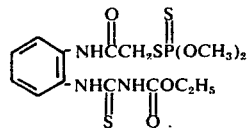

7. The thioureidobenzene compound as claimed in claim 2, which is

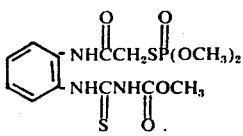

8. The thioureidobenzene compound as claimed in claim 2, which is

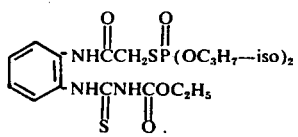

* * * * *